United States Patent

Vinogradov et al.

[11] Patent Number: 5,837,865
[45] Date of Patent: Nov. 17, 1998

[54] PHOSPHORESCENT DENDRITIC MACROMOLECULAR COMPOUNDS FOR IMAGING TISSUE OXYGEN

[75] Inventors: Sergei A. Vinogradov; David F. Wilson, both of Philadelphia, Pa.

[73] Assignee: Trustees of the University of Pennsylvania, Philadelphia, Pa.

[21] Appl. No.: 767,158

[22] Filed: Dec. 16, 1996

Related U.S. Application Data

[63] Continuation-in-part of Ser. No. 137,624, Oct. 15, 1993.
[51] Int. Cl.⁶ .............................. A61B 5/00; C07D 478/22
[52] U.S. Cl. ............................................ 540/145; 128/654
[58] Field of Search .............................. 540/145; 128/654

[56] References Cited

U.S. PATENT DOCUMENTS

| | | | |
|---|---|---|---|
| 4,289,872 | 9/1981 | Denkewalter et al. | 528/328 |
| 4,507,466 | 3/1985 | Tomalia et al. | 528/332 |
| 4,558,120 | 12/1985 | Tomalia et al. | 528/363 |
| 4,568,737 | 2/1986 | Tomalia et al. | 528/332 |
| 4,587,329 | 5/1986 | Tomalia et al. | 528/363 |
| 4,631,337 | 12/1986 | Tomalia et al. | 528/391 |
| 4,947,850 | 8/1990 | Vandekooi et al. | 128/654 |
| 5,041,516 | 8/1991 | Frechet et al. | 528/44 |
| 5,098,475 | 3/1992 | Winnik et al. | 106/22 |
| 5,256,193 | 10/1993 | Winnik et al. | 106/21 A |
| 5,393,795 | 2/1995 | Hedstrand et al. | 521/134 |
| 5,393,797 | 2/1995 | Hedstrand et al. | 521/134 |
| 5,418,301 | 5/1995 | Hult et al. | 525/437 |

OTHER PUBLICATIONS

Jin et al., J. Chem. Soc., Chem. Commun. 1990 pp. 1260–1263.

*Primary Examiner*—Mukund Shah
*Assistant Examiner*—Pavanaram K. Sripada
*Attorney, Agent, or Firm*—Duane, Morris & Heckscher LLP

[57] ABSTRACT

This invention relates to phosphorescent probes effective for oxygen measurement in human or animal tissue comprising a porphyrin chromophore capable of releasing absorbed energy as phosphorescent light and a dendrimer, wherein said porphyrin chromophore comprises the core of the dendrimer.

18 Claims, 8 Drawing Sheets

5,837,865

PHOSPHORESCENT DENDRITIC MACROMOLECULAR COMPOUNDS FOR IMAGING TISSUE OXYGEN

RELATED APPLICATIONS

This application is a continuation-in-part of application Ser. No. 08/137,624, filed Oct. 15, 1993.

FIELD OF THE INVENTION

The present invention relates to oxygen measurement in human and animal tissue, and more particularly to novel phosphorescent probe molecules.

BACKGROUND OF THE INVENTION

The reliable and accurate measurement of the oxygen supply in mammal tissue is important to ensure that the supply is adequate as the circulatory system employs specialized oxygen-carrying molecules in the blood to deliver oxygen from the lungs to other tissues throughout the body. Thus, to function normally, every organ in the body must contain sufficient amounts of oxygen in every tissue. Therefore, differing oxygen levels in tissue can be indicative of tissue structure abnormalities, defects, whether caused externally or are genetic, or of disease.

Methods of determining tissue oxygen concentration/oxygen partial pressure by measuring the quenching effect of oxygen on molecular phosphorescence of organic compounds are known. See, for example, U.S. Pat. No. 4,947,850. See also, for example, U.S. application Ser. No. 08/137,624, filed Oct. 15, 1993, which is incorporated herein by reference.

For phosphorescent compounds to be suitable for use as a phosphorescent oxygen probe (hereinafter "phosphor") in determination of tissue oxygenation, it is desirable that (1) the compounds have high absorbance in the near infrared region of the spectrum where natural chromophores of tissue, such as hemoglobin or myoglobin, have only very weak absorption; (2) compounds have phosphorescence with high quantum yields at room temperature, preferably greater than 2%; and (3) also have suitable lifetimes, preferably from about 0.1 to about 1 msec.

Phosphorescent probes should also be non-toxic or of negligible toxicity, substantially chemically inert to body fluids and components, easily excretible, and should also be of sufficient solubility in body physiological media such that oxygen molecules can approach close enough for efficient quenching, and provide reliable and accurate oxygen measurements.

Generally, the surrounding environment of such oxygen probes influence whether the probe has one or more of the aforesaid desirable properties. In accordance with this invention, "the surrounding environment" comprises such factors as atoms, various functional groups, various proteins, enzymes and other macromolecules in the environment of the phosphor which determine such properties of the phosphor relative to oxygen measurement, including, but not limited to, water solubility, toxicity, oxygen quenching constant, sensitivity to chemically active components of tissue, and ease of excretion from the body through the kidney.

It is desirable to limit the aforesaid diverse factors of the surrounding environment by creating an inert globular structure around the phosphor which only small unchanged molecules can approach close enough for efficient quenching, i.e. oxygen, while also possessing the aforesaid desirable properties of a phosphor.

A new class of phosphors suitable for oxygen measurement has recently been reported in Vinogradov and Wilson, *J. Chem. Soc., Perkin Trans.* 2, 103–111 (1995), and in the aforementioned U.S. application Ser. No. 08/137,624, both of which are complexes of Group III metals, such as Pd and Pt, with extended porphyrins, such as, for example, tetrabenzoporphyrin, tetranaphthaloporphyrin, tetraanthraporphrin and various derivatives thereof. Pd complexes of tetrabenzoporphyrins and tetranaphthaloporphyrins are especially desirable as they show strong light absorption in the near IR region (610–650 nm and 700–720 nm, respectively) where tissue is practically transparent. Further, Pd tetrabenzoporphyrins (PdTBP) and their derivatives have been shown to have long-lived phosphorescence (~250 msec) with quantum yields of 8–10%.

It is therefore an object of this invention to further improve on the structure of such compounds as phosphorescent probes by modification with chemically active functional groups, and to provide a desirable surrounding environment around such phosphors to increase solubility and selectivity for interaction with molecular oxygen in mammalian tissue.

SUMMARY OF THE INVENTION

The present invention provides phosphors comprising metallo complexed extended porphyrin compounds which are complexed with dendrimers to surround the phosphors by supramolecular structures which are highly water-soluble in a wide pH range, easily excretable from the blood of mammals through the kidney, and provide additional sought-after characteristics of phosphorescent probes such as long-lived phosphorescence and suitable quantum yields.

This invention will be more fully understood from the following detailed description of preferred embodiments, drawings and examples, all of which are intended to be for illustrative purposes only, and not intended in any way to limit the scope or spirit of the claims of this invention.

DETAILED DESCRIPTION OF PREFERRED EMBODIMENTS OF THE INVENTION

Figure 1:
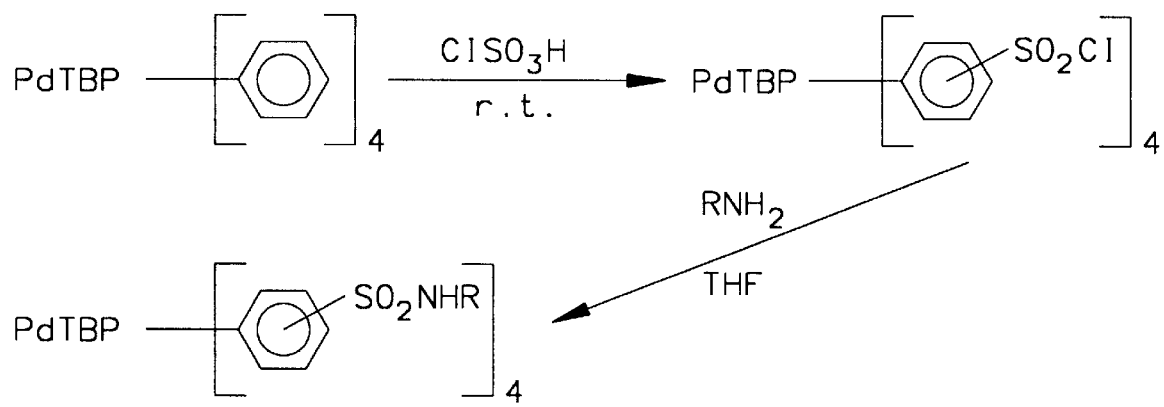
FIG. 1 illustrates an exemplanary embodiment for the production of PdTBP and PdTPTPB functionalized derivatives, for initiating divergent dendrimer growth.

The present invention provides highly efficient and highly soluble phosphorescent probes suitable for measurements of oxygen in tissue of animals and humans. The inventive probes are surrounded by an inert globular structure, an example of which is derivatized PdTBD surrounded by three-dimensional supramolecular structure known as a dendrimer.

As is well known, one of the most effective methods to build a three-dimensional supramolecular structure around a functionalized core, such as a derivitized phosphor, is by dendritic polymer growth. Dendrimers are three-dimensional supramolecular radial symmetrical molecules comprised as an initiator core, such as nitrogen, polyfunctional amines such as ethylenediamine, or in the present invention the oxygen-measuring phosphors, with interior layers attached to the core which are comprised of, for example, three or four arms with each arm being composed of repeating units, and with the number of repeating units in each arm considered to be a generation of the dendrimer. The outermost generation typically contains terminal functional groups, such as a primary amine attached to the outermost generation. The size and shape of the dendrimer molecule, and the functional groups present therein can be controlled by the choice of the initiator core, the number of generations, and the nature of the repeating units employed at each generation. For example, the chemical functionality of the repeating units in the interior layers can be, amidoamines, such as diethylene diimine, and with terminal functionalities, such as, for example, amino groups, hydroxyl groups, carboxylic acid groups, carboxylates and the like. See Urdea et al., *Science* 261: 534 (1993) and Frechet, 263: 1710–1715 (1994). Therefore, dendrimers are combinations of monomeric units which allow branching at each step of polymerization. As shown, for example, by Blumen et al., *Angewandte Chemie, Int.*, Ed. Eng. 29: 113–125 (1990), dendrimers tend to form globular structures with increasing numbers of monomeric units, which eventually will cover the centralized functional entity or compound. See also, for example, Winnik et al., U.S. Pat. No. 5,256,193.

At least two methods are known for the synthesis of dendrimer polymeric structures: the convergent and divergent growth approaches, respectively. Both are contemplated for use in the present invention.

In the convergent dendrimer synthetic route, polymer synthesis is initiated from the periphery and ends by linking branched fragments to a central core. For a detailed description of the convergent synthetic method, see Hawker et al., *J. Am. Chem. Soc.* 114: 8405–8413 (1992), Wooley et al., *J. Chem. Soc. Perkin Transactions* 1: 1059–1076 (1991), and Frechet et al., U.S. Pat. No. 5,041,516, all of which are incorporated herein by reference.

It has recently been reported that the convergent synthetic route is useful in the modification of porphyrins, i.e., producing a dendritic molecule with a core having photochemical functionality. See, Jin et al., *J. Chem. Soc. Chem. Commun.* 1260–1262 (1993). This reference describes measuring quenching of fluorescence of a Zn porphyrin encapsulated in a dendritic cage, and that the dendrimer polymeric structure provides good protection for the porphyrin core, serving as a barrier for large molecules while allowing access to smaller species.

The more typically used divergent synthetic method employs a reverse order of synthesis which involves an initial reaction of a monomer with an initiator core, followed by successive reaction of the resulting functional groups with a difunctional compound, such as a diamine, to provide the next generation of reactive amino groups such that layers of monomeric units are added to a central core sequentially until the desired degree of branching is achieved. A detailed explanation of this method can be found, for example, in Tomalia et al., *Angewandte Chemie, Int.*, Ed. Eng. 29: 138–175 (1990) and Tomalia et al., *Macromolecules* 19: 2466–2468 (1986), which are also incorporated by reference herein.

Other references relating to dendritic macromolocules and their methods of production can be found in U.S. Pat. Nos. 5,418,301; 4,568,737; 5,393,795; 5,256,193; 5,393, 797; 5,393,795; 5,393,797; 5,098,475; 5,041,516 and 4,568, 737, the entire disclosures of which are incorporated herein by reference.

As described below, in one aspect of this invention, one-, two-, and three-layer polyglutamate dendritic cages synthesized divergently around novel derivatized metallo extended porphyrin oxygen-measuring phosphor compounds results in phosphors which are highly water-soluble in a wide pH range; excretable from the blood of mammals (mice) by filtration thereof through the kidney; and display narrow distribution of phosphorescence lifetimes in deoxygenated water solutions.

As further shown below, the combination of the novel phosphor derivatives with dendrimers which are used as the phosphor's surrounding environment, provides a novel class of phosphorescent probes for accurate and reliable oxygen measurements in mammal tissue.

The phosphors employed in the present invention are fully described in copending U.S. application Ser. No. 08/137,624 and Vinogradov and Wilson, *J. Chem. Soc., Perkin trans.* 2:103–111 (1995), and preferably are of the following formula:

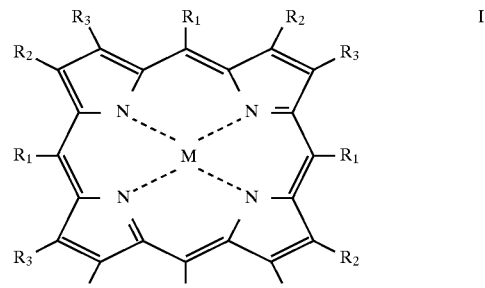

where $R_1$ is Hydrogen or substituted or unsubstituted aryl; $R_2$ and $R_3$ are independently hydrogen or are linked together to form substituted or unsubstituted aryl; and M is $H_2$ or a metal.

As is apparent to those skilled in the art, when $R_2$ and $R_3$ are linked together to form an aryl system, the aryl system is necessarily in a fused relationship to the respective pyrrole substrate.

Preferably, M is a metal selected from the group consisting of Lu, Pd, Pt, Zn, Al, Sn, Y and La, and derivatives thereof, with Pd, Pt and Lu being most preferred. Non-limiting examples of suitable metal derivatives include, Pd tetrabenzoporphyrin (PdTBP), Pd tetraphenyltetrabenzoporphyrin (PdTPTBP), and PtTBP, PtTPTBP, LuTBP and LuTPTBP and naphthaloporphyrins, such as, for example, LuTNP and PdTPTNP, all of which are described in U.S. Ser. No. 08/137,624.

In certain preferred embodiments, the phosphors of the present invention are tetrabenzoporphyrin (hereinafter "TBP") compounds, which correspond to the compound of formula I above wherein vicinal $R_2$ and $R_3$ groups are linked together to form benzene rings which are fused to the respective pyrrole rings. Also preferred are tetranaphthoporphyrin (hereinafter "TNP") and tetraanthraporphyrin (hereinafter "TAP") compounds wherein vicinal $R_2$ and $R_3$ groups are linked together to form naphthalene and anthracene ring systems, respectively. As with the fused benzene rings, the naphthalene and anthracene ring systems are fused to the respective pyrrole rings.

Unless indicated otherwise, or unless apparent from the disclosure, further reference herein to "TBP" compounds is understood to refer also to TNP and TAP compounds.

Preferred TBP compounds have the following formula

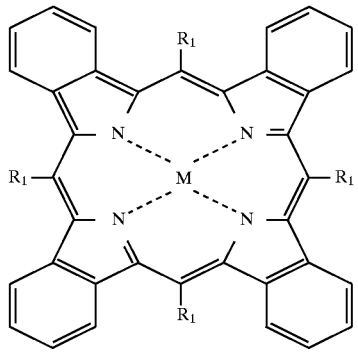

II wherein $R_1$ and M are as defined above. Particularly preferred TBP compounds are metallotetrabenzoporphyrin (hereinafter "MTBP") compounds where M is a metal or metal derivative as described hereinbefore.

Particularly preferred among the TBP compounds are the compounds of formula IV above where at least one of $R_1$ is substituted or unsubstituted phenyl. These compounds are referred to hereinafter as phenyltetrabenzoporphyrin (hereinafter "PhTBP") compounds. Preferred PhTBP compounds include substituted or unsubstituted tetraphenyltetrabenzoporphyrin (hereinafter "TPTBP") compounds, including meso-tetraphenyltetrabenzoporphyrin (hereinafter "m-TPhTBP") compounds, which have the following formula:

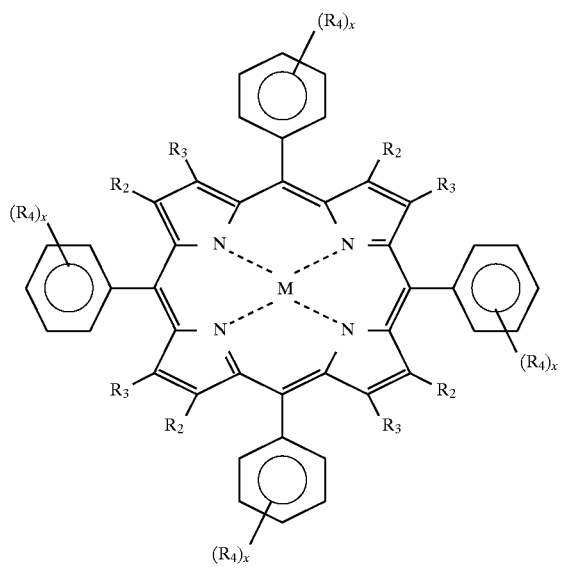

where $R_2$, $R_3$ and M are as defined above, $R_4$ is a substituent group, and x is an integer from 0 to 3. Particularly preferred TPTBP compounds are substituted compounds of formula V where x is an integer from 1 to 3.

With respect to preferred substituted compounds of the invention, substituent groups are desired which impart such desirable properties to the compounds as solubility in polar solvents, including aprotic solvents, such as dimethylformamide (DMF), acetone and chloroform ($CHCl_3$), and protic solvents, such as water. The degree of substitution and the nature of the substituent groups may be tailored to obtain the desired degree of solubility and in the desired solvent or solvent mixture.

EXAMPLES OF PREFERRED EMBODIMENTS

The preparation of the phosphorescent oxygen probes of the present invention is illustrated below by the following preferred synthetic embodiment. First, synthesis of PdTBP derivatives with chemically active functional groups is carried out to allow for further addition of dendritic fragments. Next, the actual layer-by-layer divergent growth of the dendrimer polymeric structure around the porphyrin core is accomplished to form the completed probe.

An alternate embodiment of convergent synthesis of the branched dendritic fragments, followed by attachment to a control porphyrin moiety is also contemplated.

Functionalizing a (Pd)TBP into (Pd)MCTBP

TBP and tetraphenyltetrabenzoporphrins (TPTBP) for use in this invention can be synthesized by the template condensation of potassium phthalimide with phenylacetate in the presence of Zn salts, according to the method reported by Kopranenkov et al., J. Gen. Chem. (Russ.) 51: 2165–2168 (1981) and Ichimura et al., Inorg. Chim. Acta. 182: 83–86 (1991). Tetratoluyltetrabenzoporphyrin can also be synthesized in approximately 10% yield by using 4-methylphenylacetate as a condensing agent. See, for example, Kopranenkov et al. (1981). However, as both TBP and TPTBP compounds do not contain functional groups suitable for further modification, functional groups must be added to the formed TBP and TPTBP structures.

General approaches for modification of TBP and TPTBP in accordance with this invention include a) electrophilic substitution (chlorosulfation, nitration, etc.) of phenyl rings in TPTBP's, and b) electrophilic substitution, such as nitration, of meso-positions of non-substituted TBP followed by reduction and attachment of 1,3,5,- tricarboxylic acid fragments.

It is known that phenyl rings of TPTBP and PdTPTBP are most active in electrophilic substitution reaction. See, for example, Vinogradov and Wilson, J. Chem. Soc., Perkin Trans. 2: 103–111 (1995). Such reactions, however, are not always very selective and can lead to non-selectively modified probes, with substitution occurring in either the ortho or para-positions of phenyl substituents, with the resulting production of a variety of regio- and stereo-isomers which are present in the reaction products. As exemplified below in FIG. 1, chlorosulfation of PdTPTBP leads to a mixture of tetra substituted chlorosulfonate-PdTPBP, each of which can then react with different amines to initiate divergent dendrimer growth.

It has also been shown that PdTPTBP can be readily chlorosulfated and converted into the corresponding sulfonamide with aminopolyethyleneglycols. See Vinogradov and Wilson (1995).

Figure 2:
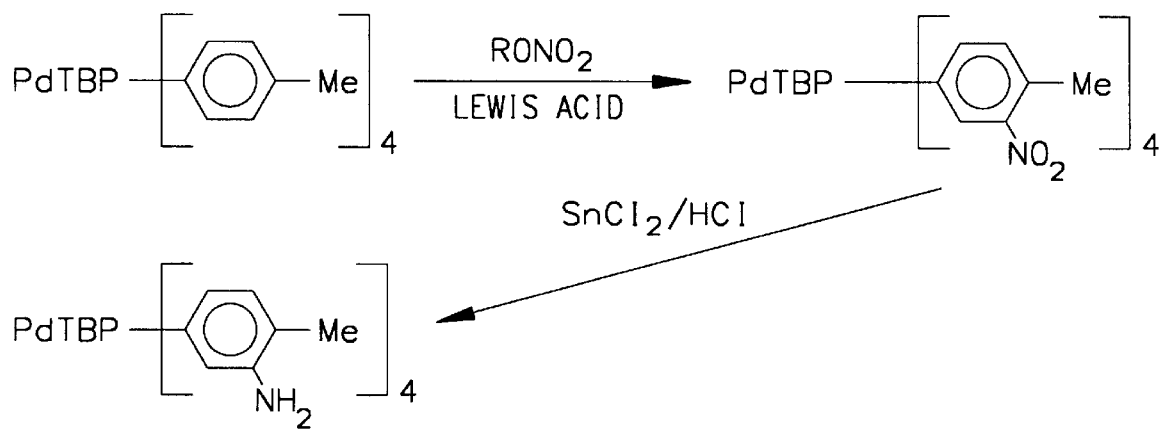
FIG. 2 illustrates another exemplary embodiment for the production of PdTBP and PdTPTPB functionalized derivatives for initiating divergent dendrimer growth.

In accordance with this invention, it is also contemplated that the employ of phenyl rings substituted with methyl groups will significantly decrease the number of isomers formed in electrophilic substitution due to steric restrictions, especially when soft electrophiles are used for modification, thereby increasing selectivity. Therefore, in accordance with this invention it is contemplated that nitration of Pd tetratoluyltetrabenzoporphyrin with agents such as esters of nitric acid in presence of weak Lewis acids such as $LnCl_3$, $ZnCl_2$ or zeolites will lead to only one regioisomer, Pd tetra(4-methyl-3-nitrophenyl)tetrabenzoporphyrin. This can then be reduced to the corresponding amino derivative (FIG. 2). Separation of the stereoisomers can be performed chromatographically and methods have been described previously for meta- and orth-tetra-aminophenylporphyrins. See Rose et al. "Large-scale preparation of $\alpha$, $\beta$, $\alpha'$, $\beta'$-atropoisomer of meso-tetrakis (0-aminophenyl) porphyrin, J. Org. Chem., 58:5030–5031 (1993).

Figure 3A:
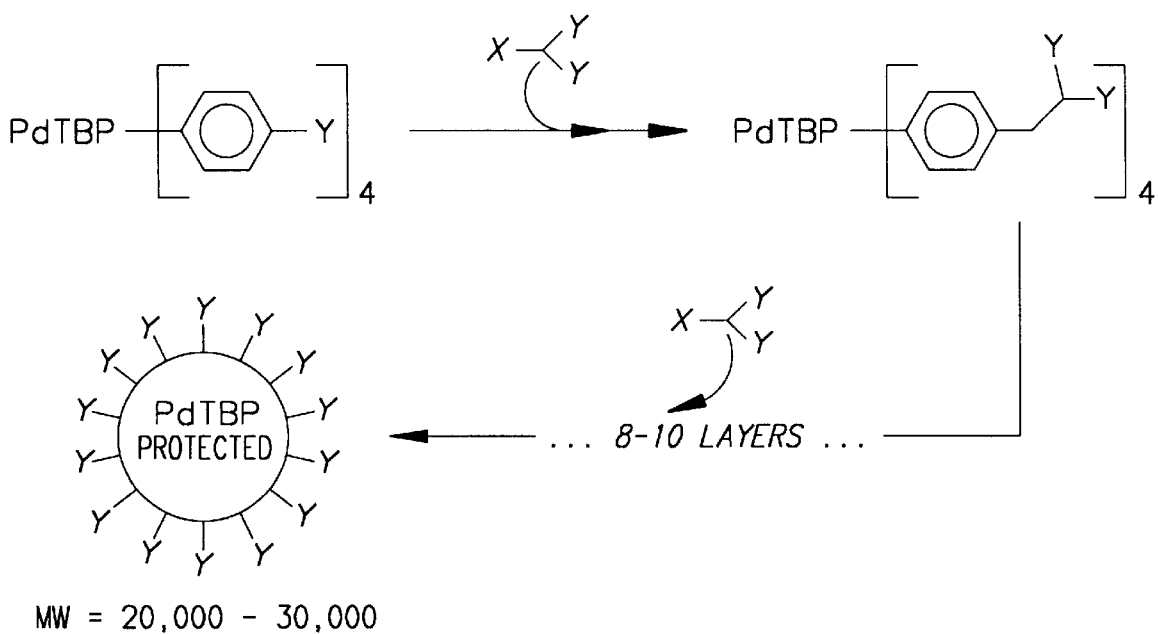
FIG. 3a illustrates the production of dendrimer growth on a core functionalized porphyrin with functional groups located at the para-positions of meso-phenyl rings.

Molecular-mechanics simulations carried out with MacroModel (Unix Version 3.5, MM2 force field) in accordance with that reported in Mohamadi et al., J. Comput. Chem. 11: 440 (1990) show that 6–10 layers of monomeric units, such as glutamates, are preferably added to a porphyrin if the initial functional groups are located at the para-positions of meso-phenyl rings to desirably achieve good protection of the central porphyrin fragment using the divergent synthetic approach (see FIG. 3A). This leads to molecules with molecular weights of about 14,000–30,000 Daltons. However, such large species might not be very useful in practice because of difficulties in excretion from the blood stream.

Figure 3B:
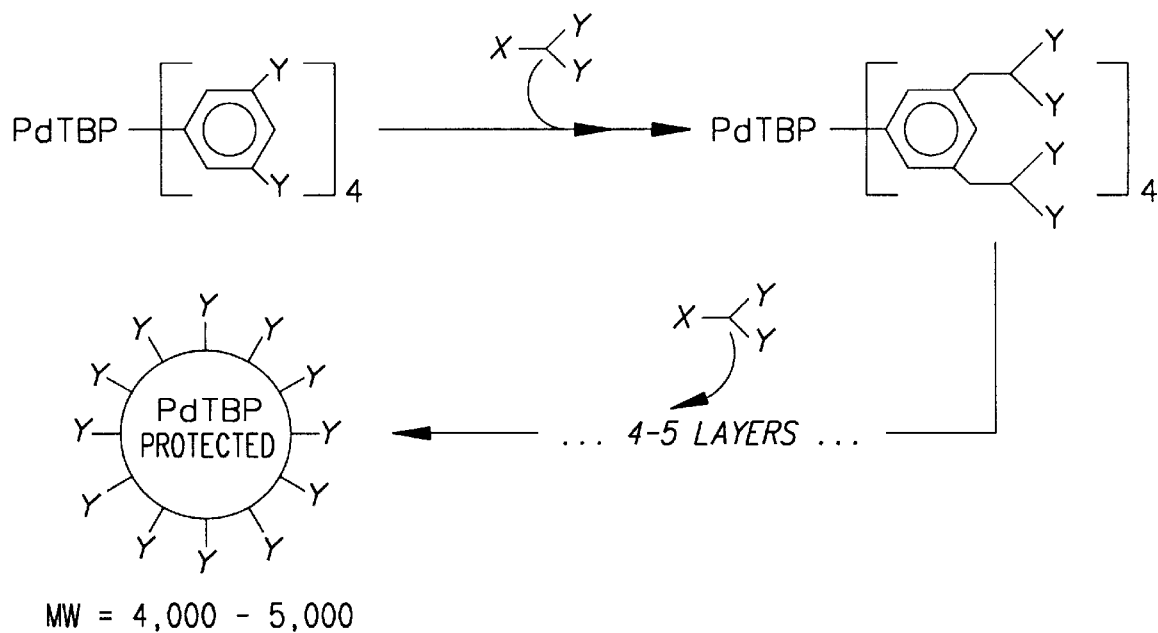
FIG. 3b illustrates the production of dendrimer growth on a core functionalized porphyrin with functional groups located at the meta-positions of meso-phenyl rings.

Further experimental data has shown that three layers decreases the oxygen quenching constant from near $2\times10^3$ $Torr^{-1}$ $sec^{-1}$ to about 750 $Torr^{-1}$ $sec^{-1}$. The latter is similar to that observed for the porphyrin bound to albumin and is suitable for measurements in vivo. Thus, it is preferable that up to four layers of glutamate will be sufficient for achieving an optimized oxygen probe. In any case, molecular modeling shows that if dendrimer growth starts from the meta-positions, globular structures form much faster and only three to five layers of monomers are needed for generation of a fully globular structure (see FIG. 3b). In this case, the molecular weight of the probe molecules will be between about 4,000 and 5,000 Daltons, which is a desirable size for good penetration through the kidney filters. Thus, it is preferred that functional groups be introduced selectively into the meta-positions of the meso-phenyl substituents.

However, it is contemplated that the porphyrin moiety will direct electrophilic substitution to the para- and orth-positions of the phenyl rings.

Figure 4A:
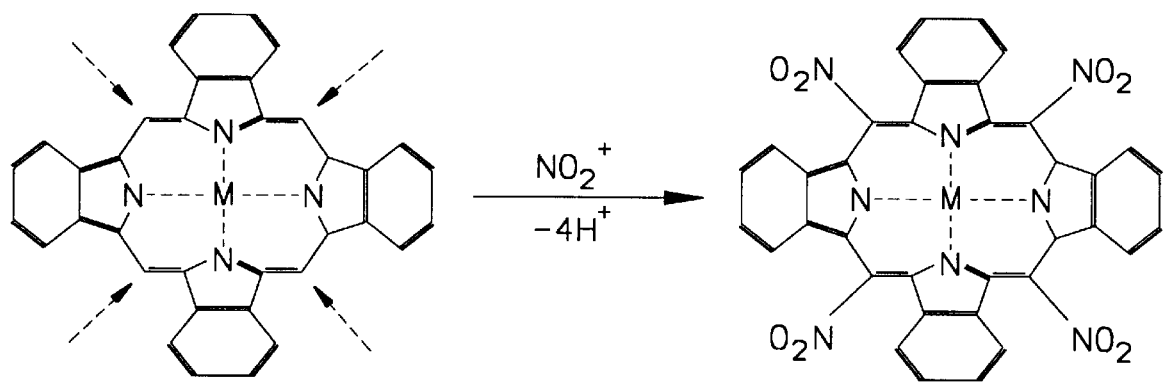
FIG. 4a illustrates a preferred embodiment of the invention of the production of a functionalized PdTBP with meta- (or psuedo meta-) functional groups by direct nitration of non-substituted TBP into meso-positions to produce (Pd) teranitrotetrabenzoporphyrin (PdTNTBP).

In a further embodiment of this invention, another reaction pathway to achieve formation of PdTBP with meta- (or pseudo meta-) functional groups is provided. This reaction is based on the direct nitration of non-substituted TBP into meso-positions, (see FIG. 4a). As shown in FIG. 4a, the arrows indicate the most probable direction for electrophilic attack. Direct nitration of porphyrins is known. See Drach et al., J. Org. Chem. 39: 3282–3284 (1974) and Bonnet et al., J. Org. Chem. 30: 2791–2798 (1965). The direct nitration of ZnTBP is also known. See Kopranenkov et al., Chem. Heter. Comp. (Russ.), 960–964 (1986). As shown in this reference, by using $HNO_3$/acetic acid and $HNO_2$/trifluoroacetic acid, up to four nitro groups can be introduced into the meso-positions of TBP cycle with yields of up to 11%.

It is also contemplated in this invention that strong ionic nitrating agents, such as, for example, $BF_4NO_2$ or highly activated covalent nitrating systems, such as, for example, $AcONO_2/BF_3.ET_2O$ and $RONO_2/TiCl_4$ be employed to increase both overall yield of nitration and the relative yield of tetranitrotetrabenzoporphyrin (TNTBP). Nitration can be carried out at the earliest state of transformation when TBP is present as its Zn complex.

Figure 4B:
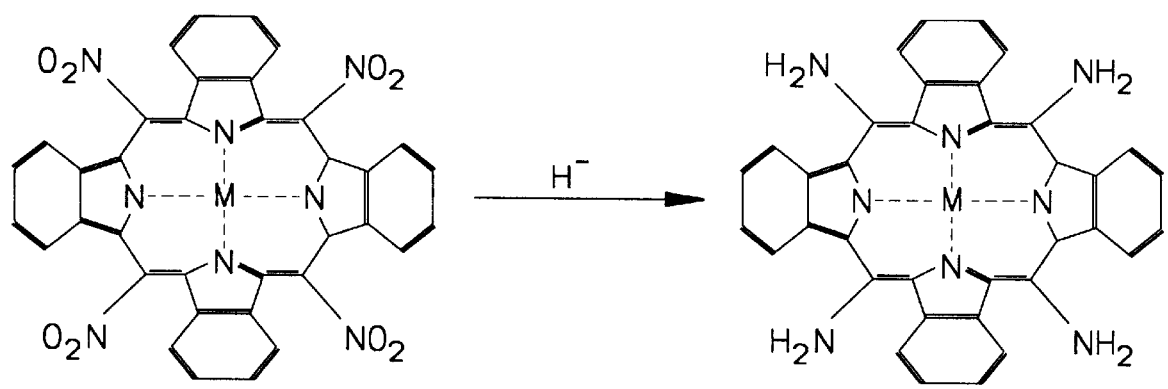
FIG. 4b further illustrates the preferred embodiment of the functionalized core porphyrin of FIG. 4a by the transformation of (Pd)TNTBP into the corresponding tetraminotetrabenzoporphyrin (TATBP or PdTATBP).

It has also been found that Zn tetranitrotetrabenzopophyrins (meso-TNTBP) can be easily demetallated by using $AcOH/H_3PO_4$ and that the insertion of Pd into TNTBP proceeds faster than into non-substituted TBP, which is due to increased non-planarity of the tetranitrated macrocycle, as confirmed using molecular-mechanics calculations (MacroModel V.3.5, MM2 force field). The reduction of TNTBP (or PdTNTBP) into corresponding tetraaminotetrabenzoporphyrin (TATBP or PdTATBP) is shown in FIG. 4b. In accordance with this invention, the resulting TATBP can be produced in good yield by preferably employing systems with increasing reducing activity, such as Zn/HCl, $SnCl_2$/AcOH, Na/MeOH, $NaBH_4$/MeOH, $LiAlH_4$/THF.

Figure 4C:
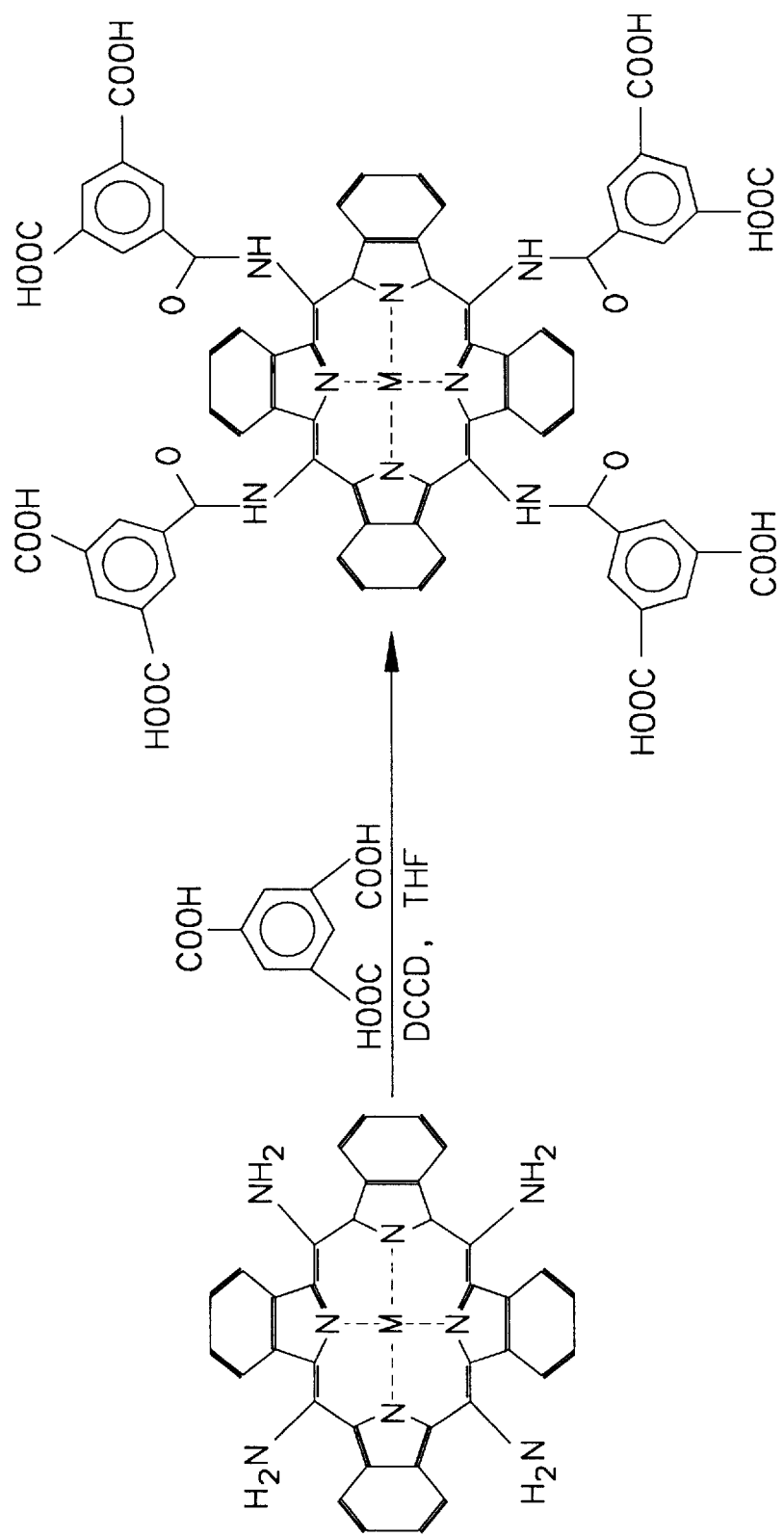
FIG. 4c further illustrates a preferred embodiment of the invention by additional functionalization of TATBP or PdTATBP in FIG. 4b with 1, 3, 5-benzenetricarboxylic acid to produce (Pd) metacarboxytetra-benzoporphyrin (MCTBP or PdMCTBP)

After formation of TATBP, further derivatization can be achieved by any of several methods employing high reactivity of the amino groups. A preferred method is amide formation between 1,3,5-benzene-tricarboxylic acid and TATBP (or PdTATBP) carried out in the presence of dicyclohehylcarbodiimide (DCCD) to produce a TBP containing pseudo meso-phenyl substituents with meta-carboxyl groups, or as termed herein, metacarboxytetrabenzoporphyrin (MCTBP). In accordance with this preferred ilustrative embodiment, MCTBP, or its Pd derivative, as shown below can be used as a core for dendritic polymer growth. See FIG. 4c.

In yet another aspect of this invention, a preferred direct synthesis of functionalized porphrins is provided which leads directly to substituted TPTBP with chemically active functionalities and suitable as a core for dendritic polymer growth. As discussed hereinabove, tetrabenzoporphrins, TBP, and tetraphenyltetrabenzoporphyrins, TPTBP, are generally synthesized by template condensation of potassium phthalimide with sodium acetate or sodium phenylacetate in the presence of Zn salts. However, due to the harsh conditions required for the template condensation, functional groups in either phthalimide or phenylacetic acid fragments usually do not survive. In accordance with the present invention, it has now been found that under modified conditions, meso-p-Br-phenyltetrabenzoporphyrins (PdTBrPTBP) and meso-p-Cl-phenyltetrabenzoporphrins (PdTClPTBP) can be synthesized directly from bromo-and chloro-phenylacetic acids. These compounds can then be converted to reactive functionalized TPTBP's by means of Pd-catalyzed cross-coupling and catalytic carbonylation. For example, with Pd catalysis, PdTPhTBP's containing Br-substituents can be converted into corresponding carboxyl compounds as follows:

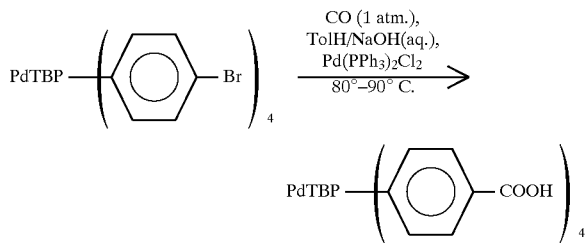

Catalytic reactions, including carbonylation and cross-coupling, for transformation of aryl halides into more reactive aryl derivitives are discussed in Colquhoun et al., "Carbonylation: direct synthesis of carbonyl compounds", Plenum Press, New York, (1991) and Heck, "Palladium reagents in organic synthesis", Academic Press, New York, (1985).

Building a Dendrimer Around (Pd)MCTBP

Dendrimers can be grown from any multi-substituted core, such as a multi-substituted porphyrins, with their different respective properties merging with increase of polymer layers. A divergent dendritic growth scheme example in accordance with this invention is conveniently shown as built around that of a functional (Pd)MCTBP core. While a convergent growth scheme is also contemplated, divergent growth is preferred as it appears to allow for more economical use of PDMCTBP and for more convenient measurements of optical and quenching properties on each step of modification. Once the necessary protection of the porphyrin is achieved, as measured by oxygen quenching constant, the addition of extra layers is not necessary; a finished probe molecule having the desired optimal size is easily synthesized.

In the present invention, any one of several known monomeric units for the formation of divergent dendrimers are useful, such as, for example, as described in U.S. Pat. Nos. 4,507,466; 4,631,337; 4,558,120; 4,568,737 and 4,587,329, and in Tomalia et al. Angewandte Chemie, Int. Ed. Eng. 29:138–175 (1990) and Tomalia et al. Macromolecules, 19:2466–2468 (1986), the entire disclosures of which are incorporated herein by reference. Other monomeric units suitable for use in the present invention for carrying dendrimer growth around a porphyrin core can be, for example, $\alpha$, $\epsilon$-L-lysine described in U.S. Pat. No. 4,289,872 and 1,3-diaminopropan-2-ol in combination with suitable $\alpha$, $\beta$-unsaturated carbonyl compound, such as described in Twyman et al. Perkins Trans. I, 407–411 (1994), which are incorporated herein by reference.

Figure 5:
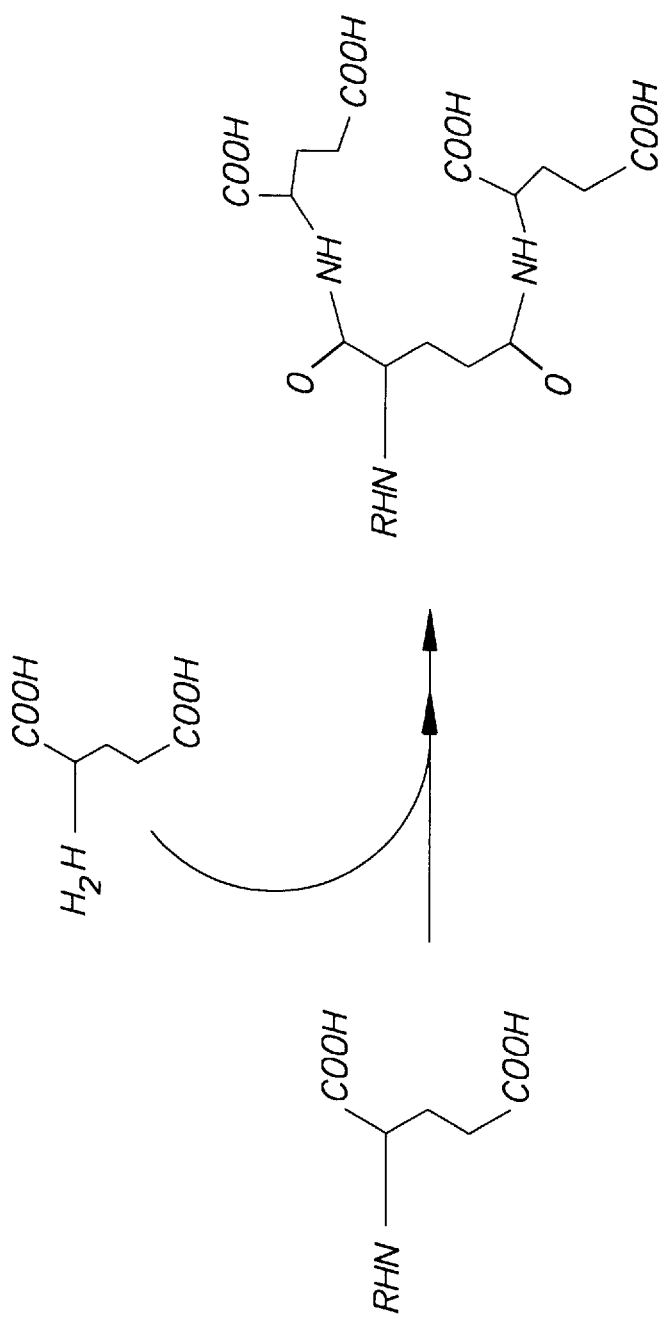
FIG. 5 illustrates the occurrence of branching in a divergent dendrimer growth mode through amide linkages formed using glutamic acid.

In a preferred embodiment of the invention, glutamic acid diallyl ester (diallylglutamate) is employed as a monomeric unit for the modification of PDMCTBP. Diallylglutamate has two protected carboxylic groups and one amino group as shown in FIG. 5. Branching and dendritic polymer formation occurs through formation of amide linkages of each step of polymer formation. It is noted that the reaction scheme in FIG. 5 is drawn for simplicity reasons, and only illustrates non-protected glutamic acid, and not diallyl-glutamate.

The reaction between the carboxyl functionalities of the porphyrin PDMCTBP (Pd-meso-tetra-(4-carboxyphenyl) porphyrin) and diallylglutamate proceeds smoothly in THF at room temperature in the presence of a 1.2 molar excess of DCCD, to produce the corresponding tetraamide in practically quantitative yield.

Figure 6:
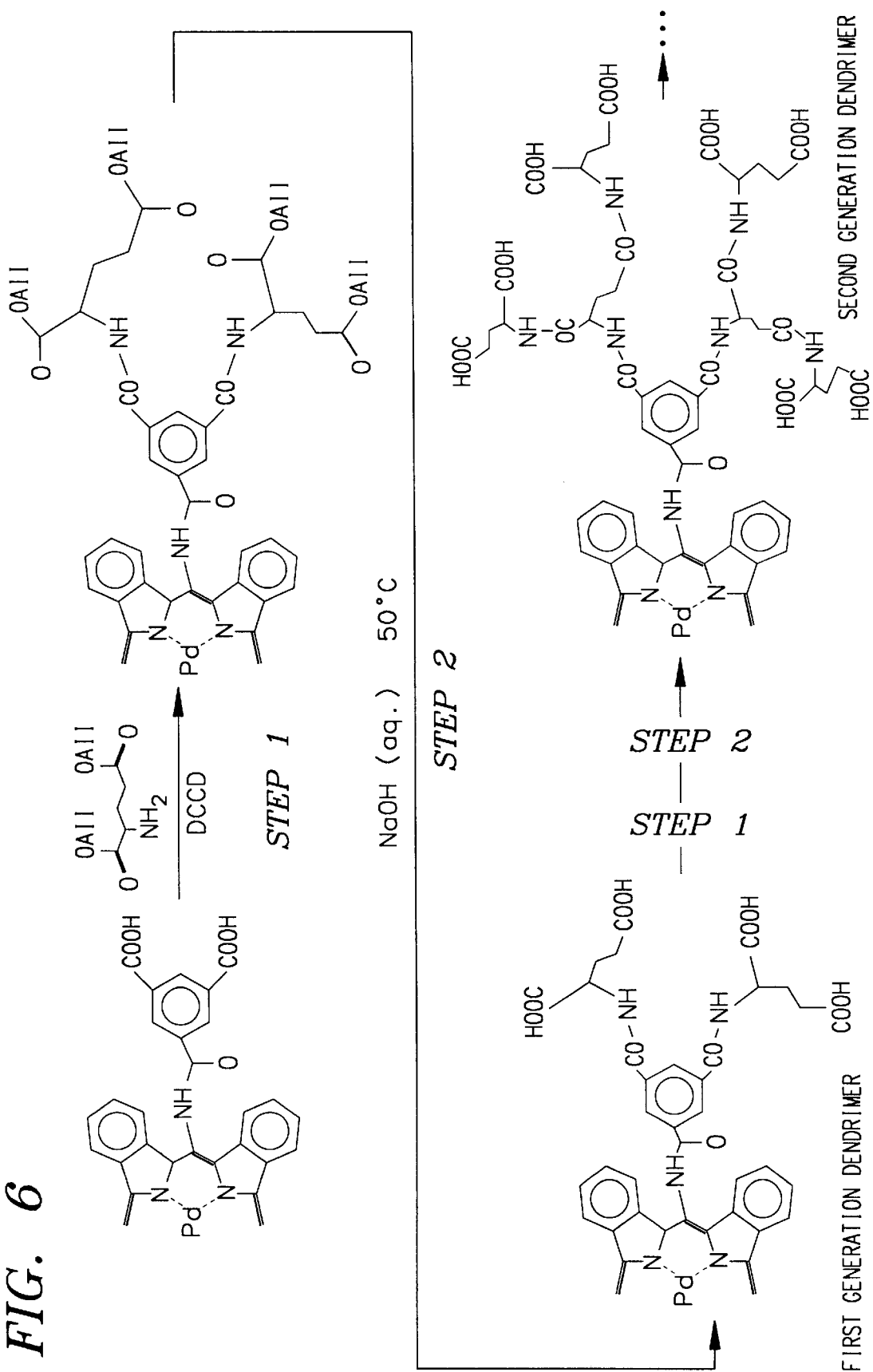
FIG. 6 illustrates a preferred embodiment of the invention of divergent dendrimer growth through two generations using MCTBP or its derivative PDMCTBP as a core porphyrin and diallylglutamate as a monomeric unit.

The allylic moiety on the introduced carboxylic groups can be readily removed by treatment of the ester with warm aqueous NaOH. Amide linkages are completely stable under these reaction conditions. Thus, hydrolysis gives porphyrin with twice as many carboxyl groups, which is ready for the addition of a new glutamate layer, or a second generation. The two first stages of the overall reaction process are shown in FIG. 6. Step 1 denotes amide linkage formation, while Step 2 denotes base catalyzed hydrolysis of the allyl ester protective groups. Purification of the final reaction product can be achieved using membrane filtration, dialysis and size exclusion chromatography, such as successfully employed for the purification of "caged" Zn porphyrin. See Jin et al., J Chem. Soc. Chem. Commun. 1260–1262 (1993).

As mentioned above, other monomeric units can be employed for dendrimer formation. These units can have protected functional groups suitable for formation of ester or ether linkages, such as frequently used in convergent dendrimer growth schemes and which are described in Hawker et al. J. Am. Chem. Soc. 112:7683–7647 (1990); and J. Am. Chem. Soc. 114: 8405–8413 (1992) Wooly et al., J. Chem. Soc. Perkin transactions 1:1059–1076 (1991), (1992), the entire disclosures of which are incorporated herein by reference.

Figure 7:
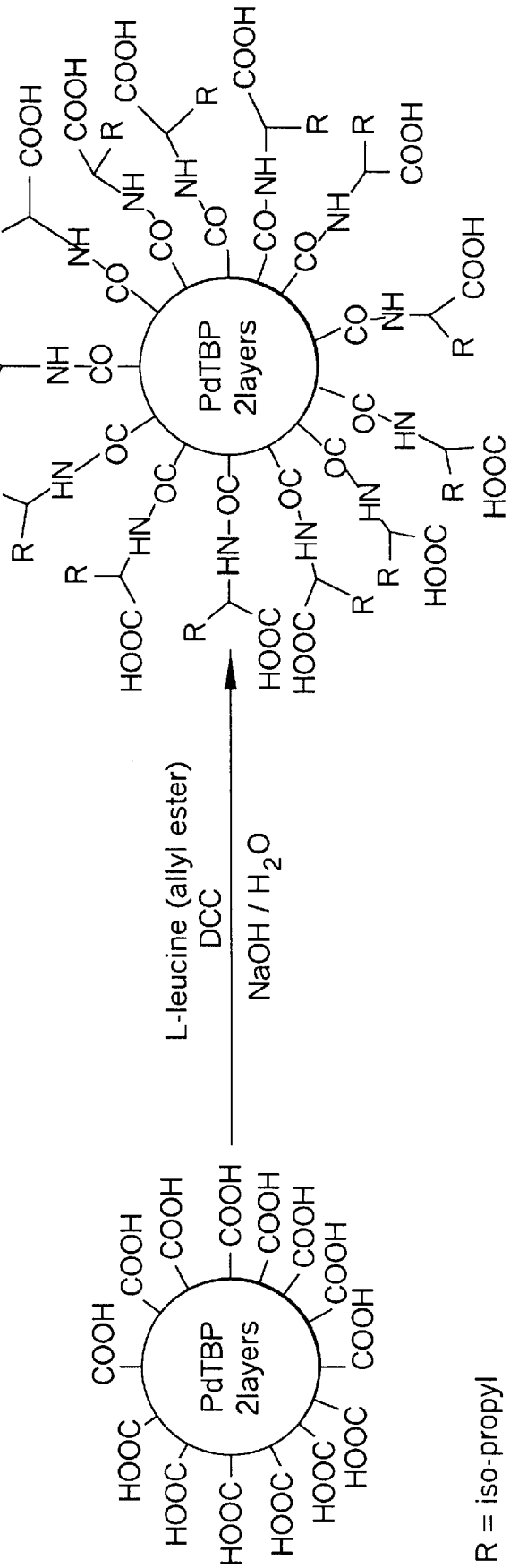
FIG. 7 illustrates a preferred embodiment of the invention of the modification of an outer layer of dendritic porphyrin.
Figure 8:
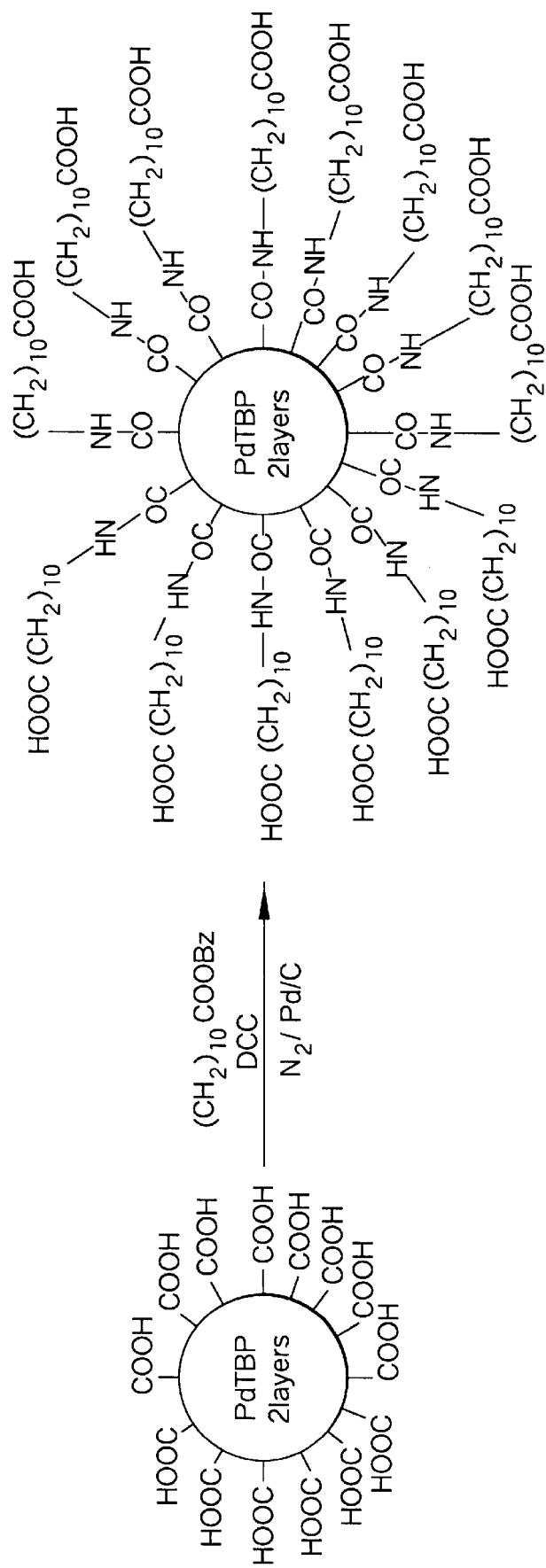
FIG. 8 illustrates another preferred embodiment of the invention of the modification of an outer layer of dendritic porphyrin.

In a further aspect of the present invention, it has been found that modification of the outer layer of dendritic porphyrins with various hydrophobic groups improves protection of core porphyrins. While not wishing to limit any aspect or portion of this invention to theory, it is thought that the addition of surface hydrophobic groups causes formation of more compact structures in water solutions, thereby decreasing oxygen quenching constants. It is also thought that hydrophobic interactions within relatively loosely packed polyamide dendrimer causes it to shrink into smaller ball-like structures of high density which prevent or at least decrease the rate of diffusion of oxygen molecules to the porphyrin core. As illustrated, for example in FIG. 7, significant protection of porphyrin can be achieved when 2-layered polyglutamate dendrimer is surface modified with L-leucine. Furthermore, lower quenching constants are observed for 2-layered polyglutamate modified with sixteen 11-aminoundecanoic acid residues. See Example 8.

We claim:

1. A phosphorescent probe effective for oxygen measurement in human or animal tissue comprising a porphyrin chromophore capable of releasing absorbed energy as phosphorescent light and a dendrimer, wherein said porphyrin chromophore comprises the core of the dendrimer.

2. The phosphorescent probe of claim 1 wherein the absorption spectrum of the chromophore exhibits strong light absorption in the near infrared region of the spectrum where natural tissue chromophores exhibit relatively weak absorption.

3. The phosphorescent probe of claim 1 wherein the absorption spectrum of the chromophore exhibits strong light absorption at from between about 600 nm to about 720 nm.

4. The phosphorescent probe of claim 1 wherein the absorption spectrum of the chromophore exhibits strong light absorption at from between about 610 nm to about 720 nm.

5. The phosphorescent probe of claim 1 wherein the porphyrin chromophore comprises a functionally derivatized metalloporphyrin.

6. The functionally derivitized metalloporphyrin of claim 5 which has the formula:

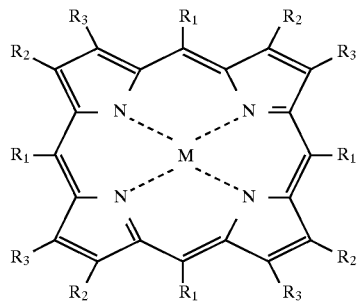

(I)

wherein:

$R_1$ is a hydrogen atom or a substituted or unsubstituted aryl;

$R_2$ and $R_3$ are independently hydrogen or are linked together to form substituted or unsubstituted aryl; and M is $H_2$ or a metal.

7. The compound of claim 6 wherein M is a metal selected from the group consisting of Zn, Al, Sn, Y, La, Lu, Pd, Pt and derivatives thereof.

8. The compound of claim 5 wherein the porphyrin is selected from the group consisting of tetrabenzoporphyrin, tetranapthoporphyrin, tetraanthraporphyrin, and derivatives thereof.

9. The compound of claim 8 wherein the metal is selected from the group consisting of Zn, Al, Sn, Y, La, Lu, Pd, Pt and derivatives thereof.

10. The compound of claim 9 wherein the derivative is a meso-tetraphenylated compound.

11. The compound of claim 10 wherein the metalloporphyrin is tetraphenyltetrabenzoporphyrin.

12. The compound of claim 10 wherein the metalloporphyrin is (Lu) tetraphenyltetranapthoporphyrin.

13. The compound of claim 10 wherein the metalloporphyrin is meso-tetra-(4-carboxylphenyl)porphyrin.

14. The compound of claim 10 which is meso-tetraphenyltetrabenzoporphyrin.

15. The compound of claim 10 which is meso-tetraphenyltetranapthoporphyrin.

16. The compound of claim 8 wherein the porphyrin is tetrabenzoporphyrin.

17. The compound of claim 10 wherein said dendrimer is a first, second, third, fourth or fifth generation dendrimer.

18. The compound of claim 17 wherein said dendrimer comprises polyglutamate dendritic cages.

* * * * *